(12) United States Patent  (10) Patent No.: US 6,172,355 B1
Gast et al.  (45) Date of Patent: Jan. 9, 2001

(54) IN-LINE INSPECTION OF CONTAINERS (75) Inventors: Terry L. Gast, Northwood; John L. Waugaman, Perrysburg; Tim Nicks, Maumee, all of OH (US); Sherwood L. Goff, Jr., Clarion; David R. Rosenquest, Summerville, both of PA (US); Ronald E. Gast, Genoa, OH (US)

(73) Assignee: Owens-Brockway Glass Container Inc., Toledo, OH (US)

( * ) Notice: Under 35 U.S.C. 154(b), the term of this patent shall be extended for 0 days.

(21) Appl. No.: 09/170,709

(22) Filed: Oct. 13, 1998

(51) Int. Cl.⁷ ........................................................ G01N 9/04
(52) U.S. Cl. ..................... 250/223 B; 209/522; 209/917; 356/239.4
(58) Field of Search ............... 250/223 B; 209/522–530, 209/539, 540–545, 917, 919, 923; 356/239.4

(56) References Cited

U.S. PATENT DOCUMENTS

| | | |
|---|---|---|
| 2,446,377 | 8/1948 | Marshall . |
| 2,825,442 | 3/1958 | Carter . |
| 2,863,355 | 12/1958 | Ledingham . |
| 3,101,848 * | 8/1963 | Uhlig .................................... 209/526 |
| 3,415,350 | 12/1968 | Murphy . |
| 3,428,174 | 2/1969 | Kulig . |
| 3,848,742 * | 11/1974 | Krenmayr ........................ 250/223 B |
| 3,866,739 | 2/1975 | Sikorski . |
| 3,901,381 * | 8/1975 | Quinn ................................... 209/522 |
| 4,021,122 | 5/1977 | Krenmayr . |
| 4,464,884 | 8/1984 | Franks . |
| 4,874,940 | 10/1989 | McMeekin . |
| 4,914,289 | 4/1990 | Nguyen . |
| 5,059,031 | 10/1991 | Hamel . |
| 5,097,216 | 3/1992 | Dimmick, Sr. et al. . |
| 5,422,476 | 6/1995 | Weber et al. . |
| 5,624,021 | 4/1997 | Novak et al. . |

* cited by examiner

Primary Examiner—Stephone B. Allen (57) ABSTRACT

Apparatus for inspecting containers traveling in sequence on a linear conveyor that includes an infeed mechanism having a first endless drive belt with a portion overlying the conveyor for abutting engagement by containers in sequence traveling on the conveyor, and a first motor driving the belt at a speed greater than the speed of the conveyor for diverting containers laterally at least partially off the conveyor. An abutment assembly is disposed in opposition to the first belt for abutting engagement by containers diverted by the infeed mechanism, such that containers diverted from the conveyor and engaged between the first belt and the abutment assembly are rotated during longitudinal travel along the abutment assembly. Apparatus inspects the containers as they are rotated during travel along the abutment assembly. An outfeed mechanism is disposed adjacent to the abutment assembly for engaging containers in sequence following engagement with the abutment assembly, and for diverting the containers back onto the conveyor.

37 Claims, 10 Drawing Sheets

IN-LINE INSPECTION OF CONTAINERS

The present invention is directed to electro-optical inspection of containers, and more particularly to a method and apparatus for inspecting containers for commercial variations as the containers are transported along a linear conveyor.

BACKGROUND AND OBJECTS OF THE INVENTION

It has heretofore been proposed to employ electro-optical techniques for detecting commercial variations in containers of glass or plastic composition. The term "commercial variations" refers to variations from nominal design that may affect the commercial acceptability of the containers. Commercial variations may include, for example, variations in color or dimension from those desired by the manufacturer or customer, surface variations especially around the sealing surface of the container, or manufacturing anomalies in the container sidewall such as stress cracks or inclusions.

U.S. Pat. No. 4,874,940 discloses a method and apparatus for electro-optical inspection of containers as the containers are transported along a linear conveyor. The apparatus includes an arm that is angulated over the conveyor for engaging and laterally diverting containers as the containers are brought by the conveyor into abutment with the arm. (Directional adjectives such as "lateral" and "longitudinal" are taken with respect to the direction of linear conveyor motion, unless otherwise indicated.) The diverted containers are brought into engagement with a drive belt, which is spaced laterally from the conveyor and cooperates with a parallel section of the arm to propel the containers longitudinally over a wear plate while rotating each container about its central axis. A light source positioned beneath the wear plate directs a linear light beam through a slot in the wear plate, and through the containers as they are rotated and transported along the wear plate, onto a camera disposed above the wear plate. The camera is coupled to suitable electronics for detecting commercial variations in the containers as a function of the light energy incident on the camera. Following transport along the wear plate slot, the containers are brought into engagement with a second drive belt that is angulated with respect to the longitudinal direction of the conveyor so as to divert the containers in sequence back onto the conveyor.

Although the method and apparatus disclosed in the noted patent address problems theretofore extant in the art, further improvements remain desirable. In particular, it is an object of the present invention to provide a method and apparatus for in-line inspection of containers, of the general type disclosed in the noted patent, that reduce instability of the containers at the infeed and/or outfeed ends of the apparatus, which might otherwise lead to hesitation, stumbling and toppling of the containers, which in turn would require manual intervention by an operator to restore the inspection station to proper operation. Another object of the present invention is to provide a method and apparatus of the described character that are characterized by ease of container removal in the event of jamming or for other reasons, and that terminate operation of the inspection station in the event of a container jam. Yet another object of the invention is to provide a method and apparatus of the described character that are characterized by reduced maintenance requirements and increased operating lifetime. A further object of the invention is provide to a method and apparatus of the described character that can be readily adapted for use in conjunction with large containers—i.e., containers such as jars that have a large diameter compared with axial length. Yet another object of the present invention is to provide a method and apparatus of the described character that are characterized by ease of adjustment, and that can be adjusted during operation. Another object of the present invention is to provide a method and apparatus that achieve one or more of the foregoing objectives, and can be readily retrofitted into existing inspection installations in place of the apparatus disclosed in the noted patent.

SUMMARY OF THE INVENTION

Apparatus for inspecting containers traveling in sequence on a linear conveyor in accordance with a first aspect of the present invention includes an infeed mechanism having a first endless drive belt with a portion overlying the conveyor for abutting engagement by containers in sequence traveling on the conveyor, and a first motor driving the belt for diverting containers laterally at least partially off the conveyor. An abutment assembly is disposed in opposition to the first belt for abutting engagement by containers diverted by the infeed mechanism, such that containers diverted from the conveyor and engaged between the first belt and the abutment assembly are rotated during longitudinal travel along the abutment assembly. Apparatus inspects the containers as they are rotated during travel along the abutment assembly. An outfeed mechanism is disposed adjacent to the abutment assembly for engaging containers in sequence following engagement with the abutment assembly, and for diverting the containers back onto the conveyor.

The first endless drive belt has an elongated reach parallel to the conveyor, and an angulated infeed reach extending laterally over the conveyor for intercepting containers on the conveyor. A second drive belt preferably is operatively coupled to the first drive belt and the first motor, and is disposed in opposition to the outfeed mechanism for capturing containers therebetween and diverting the containers back onto the conveyor at substantially the speed of the conveyor. The second belt preferably is coupled by a drive arrangement to the first belt for driving the second belt at a speed less than and proportional to the speed of the first belt. The first and second belts, the first motor and the gear drive mechanism are mounted on a carriage in the preferred embodiment of the invention that is adjustably positionable with respect to the conveyor. Thus, the containers are affirmatively captured during infeed, outfeed and transport through the inspection station, which improves container handling stability.

In accordance with another aspect of the present invention, which preferably although not necessarily is implemented in conjunction with other aspects of the invention, the outfeed mechanism includes a third endless belt and a motor for driving the third belt to engage the containers and direct the containers in sequence back onto the conveyor while reducing the speed of the containers substantially to match that of the conveyor. The third endless belt and associated motor preferably are mounted on a carriage that is adjustably positionable with respect to the conveyor.

In accordance with yet another aspect of the present invention, which again may be used separately from or more preferably in combination with other aspects of the invention, the abutment assembly includes at least one abutment drag rail mounted for lateral motion in opposition to the first drive belt. The drag rail is resiliently urged toward the first drive belt for capturing containers therebetween and accommodating minor dimensional variations in the containers. The drag rail is mounted on a pair of longitudinally spaced pivot posts. The posts are engaged by associated springs for biasing the abutment drag rail toward the first drive belt, and for accommodating pivotal motion of the drag rail away from the first drive belt. Spring force on the drag rail is adjustable. A limit switch is preferably disposed adjacent to each pivot post for detecting excess pivotal motion of the drag rail away from the drive belt, and thereby indicating a possible jam of containers in the inspection apparatus. A controller is responsive to the limit switches for de-activating all drive motors. The inspection station is thus automatically shut down in the event of a container jam or other situation that results in excess motion at the drag rail. Alternatively, an operator may shut down the inspection station by manually moving the drag rail away from the drive belt. An elastic layer is disposed on the drag rail for enhanced frictional engagement with containers propelled through the inspection station. This helps ensure uniform rotation of the containers as they pass through the inspection station. A single drag rail or a vertically spaced pair of drag rails may be employed depending upon the size of the containers to be inspected.

The drag rail preferably has an angulated infeed reach that is opposed to the angulated infeed reach of the first drive belt for enhanced capture of containers therebetween, and to help prevent instability of the containers during lateral motion off of the conveyor. The longitudinal position of the infeed reach of the rails is adjustable for accommodating containers of differing diameter and to optimize operation of the apparatus. This adjustment is accomplished by means of a pair of plates coupled to the abutment rails. One of the plates has surface threads, and the other plate has a surface pocket within which an adjustment screw is disposed. Rotation of the screw with respect to the pocket and in engagement with the threads on the opposing plate thus longitudinally adjusts the plates with respect to each other, and thereby adjusts position of the drag rail infeed reach with respect to the infeed reach of the first drive belt. A second screw or other suitable means is provided for locking the plates with respect to each other when the desired adjusted position is obtained. The infeed reach of the drag rail(s) is angulated slightly as compared with the infeed reach of the drive belt for enhanced funneling of containers to the inspection station.

In accordance with yet another aspect of the present invention, the abutment assembly may comprise a drive belt and a motor for driving the belt in a direction opposite to that of the first belt. In this way, containers captured between the belts are transported longitudinally through the inspection station while being rotated at increased velocity about their axes. This aspect of the invention is particularly useful in conjunction with containers of larger diameter to ensure that the containers will be rotated at least 180°, and preferably at least 360°, during passage through the inspection station. The drive belt and associated motor preferably are mounted on a carriage that is adjustably positionable with respect to the conveyor. The carriage assembly may thus be mounted adjacent to the conveyor in place of the drag rail carriage assembly for adapting the inspection station for use in conjunction with larger containers such as jars.

A method of inspecting containers traveling on a linear conveyor in accordance with a further aspect of the present invention includes the step of positioning a first motor-driven belt overlying the conveyor to divert containers from the conveyor laterally against an abutment assembly. The containers are transported between the first drive belt and the abutment assembly at a speed greater than that of the conveyor while rotating each container through at least one-half revolution. The containers are inspected while being transported and rotated through the inspection station. The containers are then diverted in sequence between second and third motor-driven belts back onto the conveyor at a speed substantially matching that of the conveyor. The abutment mechanism may be provided either in the form of a rail assembly or a fourth drive belt, as previously described.

The various aspects of the invention provide improved handling of the containers during infeed from and/or outfeed to the linear conveyor. Specifically, and in accordance with the preferred embodiments of the invention in which the various aspects are employed in combination, the containers are captured from opposed sides during lateral diversion off of and back onto the conveyor. This greatly improves container stability by reducing any tendency for the containers to hesitate or stumble, and possibly topple to jam the apparatus. Either a spring-biased drag rail or a motor-driven drive belt assembly is disposed in opposition to the main drive belt to capture the containers during transport through the inspection station. The spring-biased drag rail is coupled to switches to detect jamming and terminate operation of the inspection station. The motor-driven belt is employed in conjunction with larger containers, which have a lesser tendency to topple and jam, and which must be rotated more rapidly during passage through the station.

BRIEF DESCRIPTION OF THE DRAWINGS

The invention, together with additional objects, features and advantages thereof, will be best understood from the following description, the appended claims and the accompanying drawings, in which:

DETAILED DESCRIPTION OF PREFERRED EMBODIMENTS

FIGS. 1–10 and 14–16 illustrate an apparatus 20 for inspecting containers 22 traveling on a linear conveyor 24 in accordance with one presently preferred embodiment of the invention. Conveyor 24 may comprise a segmented conveyor or an endless conveyor belt, for example, slidably carried on a conveyor support 26, on which apparatus 20 is removably and adjustably mounted. Conveyor 24 transports containers 22 in sequence in a longitudinal direction 28 at a first speed associated with the conveyor. Apparatus 20 (1) diverts containers 22 in sequence from conveyor 24, (2) transports the containers at increased speed along the side of the conveyor to increase spacing between the containers while rotating the containers about their axes, (3) inspects the containers for commercial variations during such transport and rotation, and (4) diverts the containers back onto conveyor 24 while terminating rotation and reducing speed substantially to match that of the conveyor.

Figure 3:
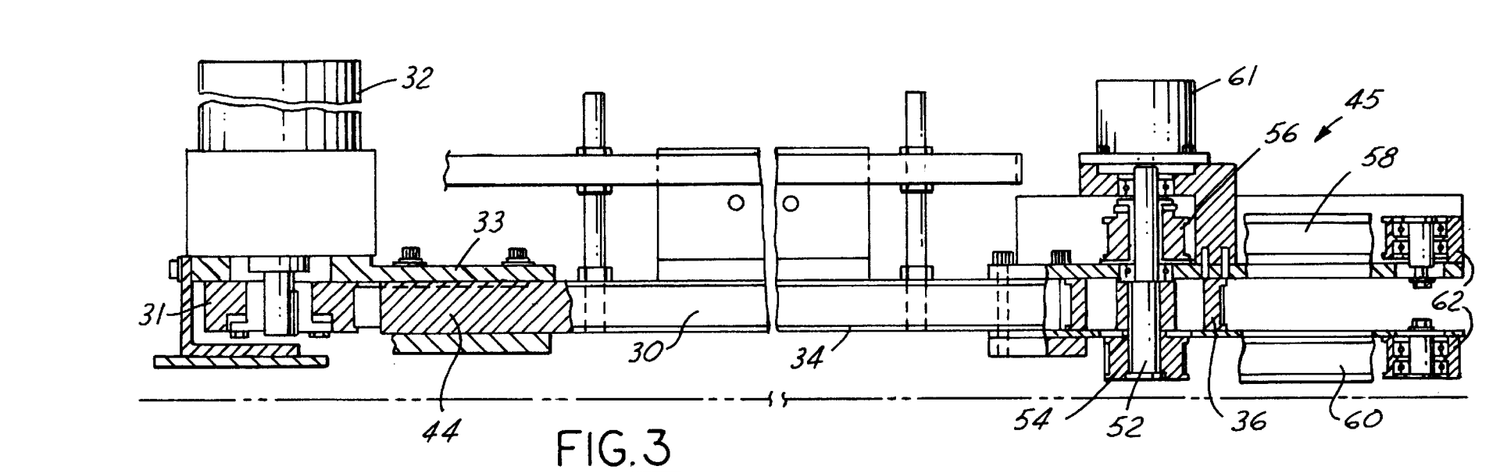
FIG. 3 is a sectional view taken substantially along the line 3—3 in FIG. 2.
Figure 4:
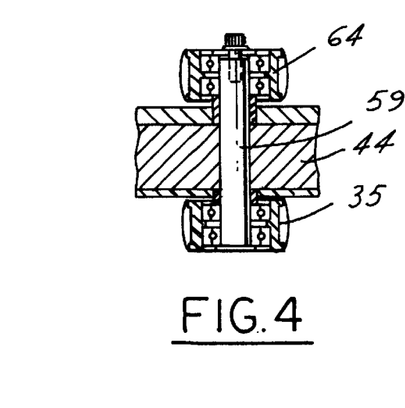
FIGS. 4 and 5 are sectional views taken substantially along the lines 4—4 and 5—5 in FIG. 1.
Figure 5:
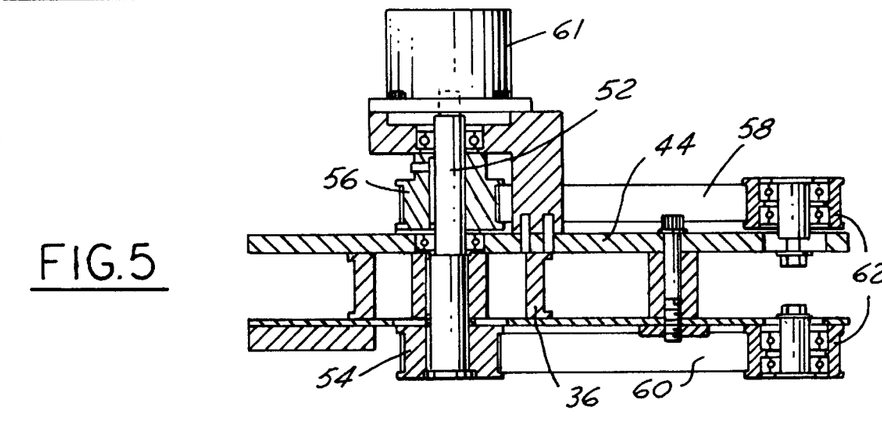
Figure 6:
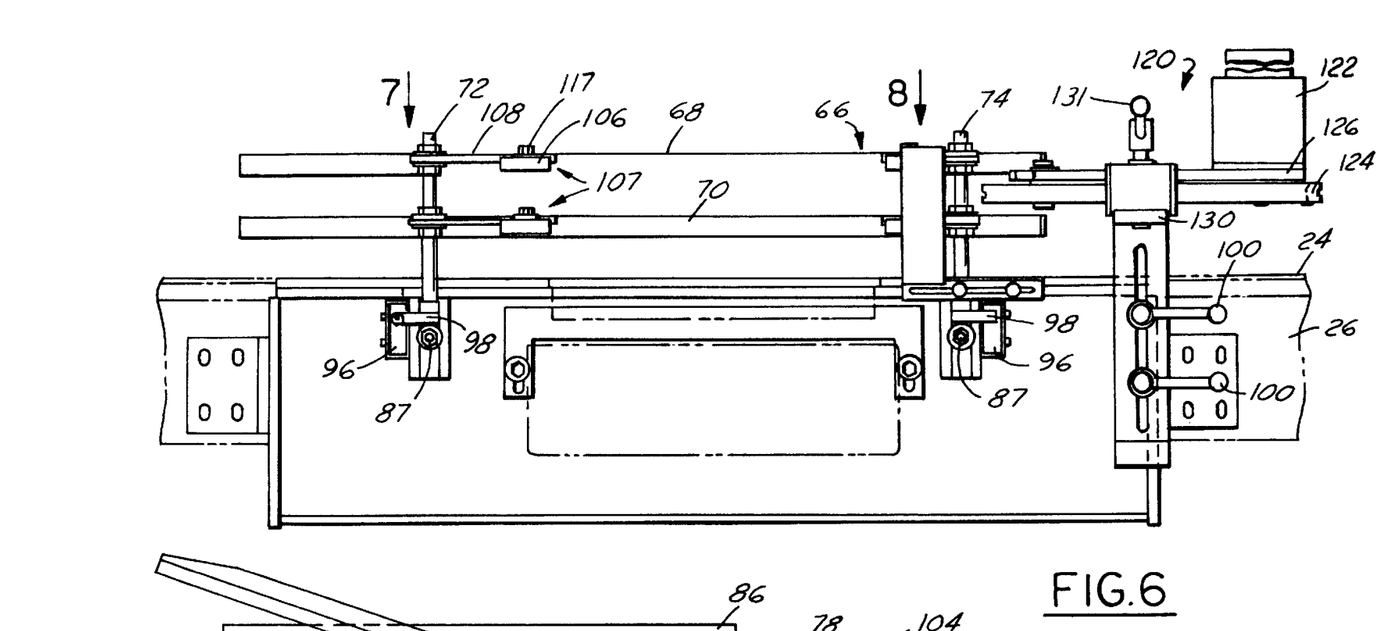
FIG. 6 is a side elevational view taken substantially from the direction 6 in FIG. 1.
Figure 7:
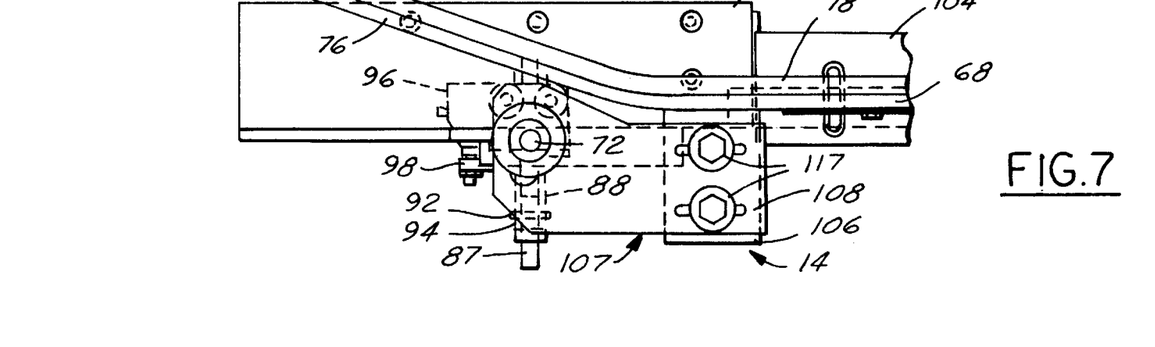
FIG. 7 is a fragmentary top plan view taken substantially from the direction 7 in FIG. 6.

Apparatus 20 includes a first endless drive belt 30 coupled to a drive motor 32 by a sprocket 31 (FIG. 3). Motor 32 is mounted on a support carriage 44 by a bracket 33. From sprocket 31, belt 30 extends along carriage 44, around a wear plate and a pulley 36, and back to sprocket 31. An inlet reach 38 of drive belt 30 is disposed over conveyor 24 and angulated with respect thereto at an acute angle to the direction 28 of conveyor motion, so that containers 22 abut belt reach 38 in sequence as they are conveyed by the conveyor.

Figure 1:
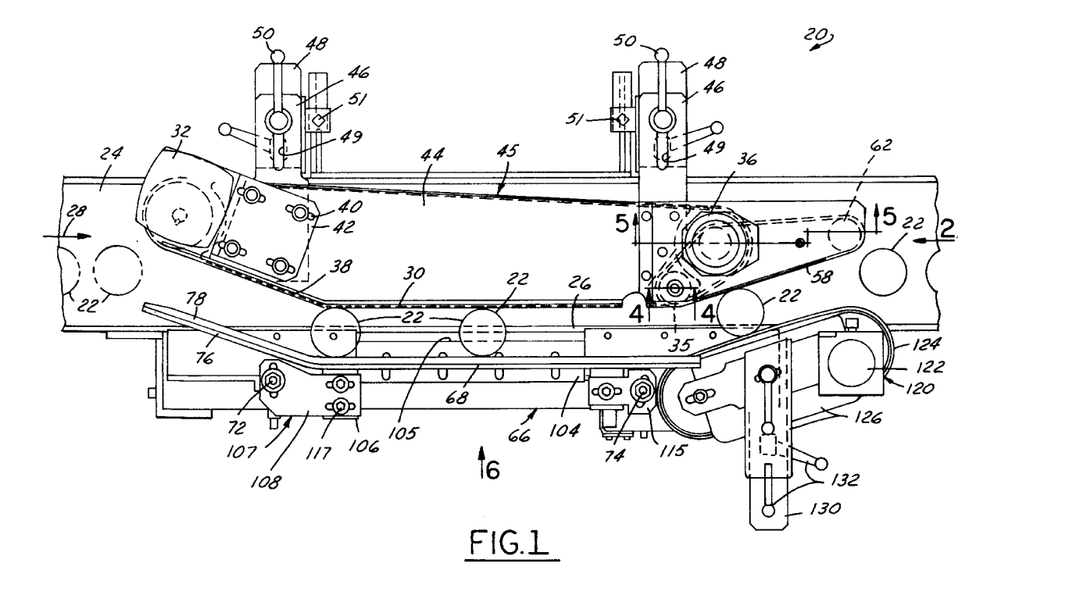
FIG. 1 is a top plan view of an apparatus for inspecting containers in accordance with one presently preferred embodiment of the invention.
Figure 2:
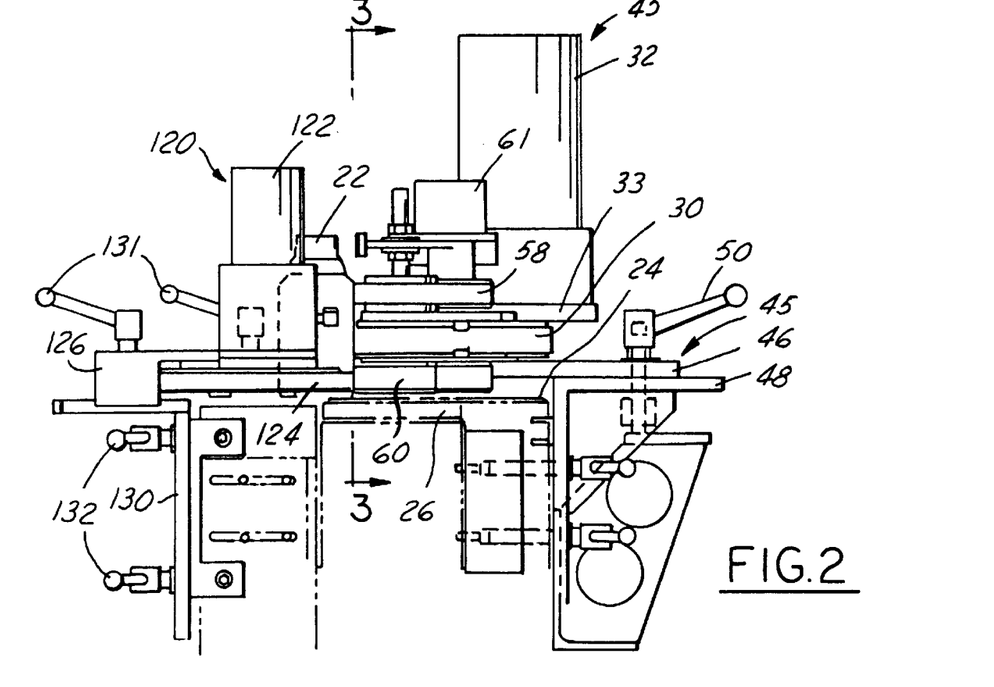
FIG. 2 is an end elevational view taken from the direction 2 in FIG. 1.

Carriage 44 has bracket arms 46 (FIGS. 1 and 2), by means of which the entire carriage assembly 45 is mounted to brackets 48 affixed to conveyor support 26 (see FIG. 2). Handles 50 releasably mount carriage bracket arms 46 on brackets 48. Brackets 48 are vertically positionable with respect to conveyor support 26 by means of the vertical jack screws 51 illustrated in FIG. 1. Slots 49 in bracket arms 46 provide for a lateral adjustment of carriage assembly 45 with respect to conveyor 24. Thus, carriage assembly 45 is vertically adjustable by means of jack screws 51 and laterally adjustable by means of handles 50 and slots 49. Tension in belt 30 is adjustable by means of slots 40 in motor bracket 42. A wear plate is provided at each location along carriage 44 at which belt 30 changes direction.

Referring to FIGS. 1 and 3–5, first drive belt 30 engages pulley 36, which is affixed to a shaft 52 rotatable on carriage assembly 45. A pair of pulleys 54, 56 are affixed to shaft 52 on opposed sides of pulley 36. A pair of vertically spaced endless outfeed drive belts 58, 60 are respectively coupled to pulleys 56, 54, and extend around idler pulleys 62, 64, 35 on carriage assembly 45. Thus, motor 32 drives belt 30, which in turn drives belts 58, 60 through pulleys 36, 54 and 56. The pulley ratios preferably are such that belts 58, 60 travel at approximately the speed of conveyor 24, while belt 30 travels at slightly more than twice the speed of the conveyor. The outfeed belt assembly is carried, along with motor 32 and belt 30, on carriage 44, and thus forms part of carriage assembly 45. Shaft 52 is coupled to an encoder 61, which in turn is connected to the control electronics (FIG. 16) to provide an indication of belt operation and speed.

Pulleys 35, 64 are coaxially mounted on a shaft 59 (FIG. 4) by associated bearings. Shaft 59 is mounted on carriage assembly 45.

Figure 8:
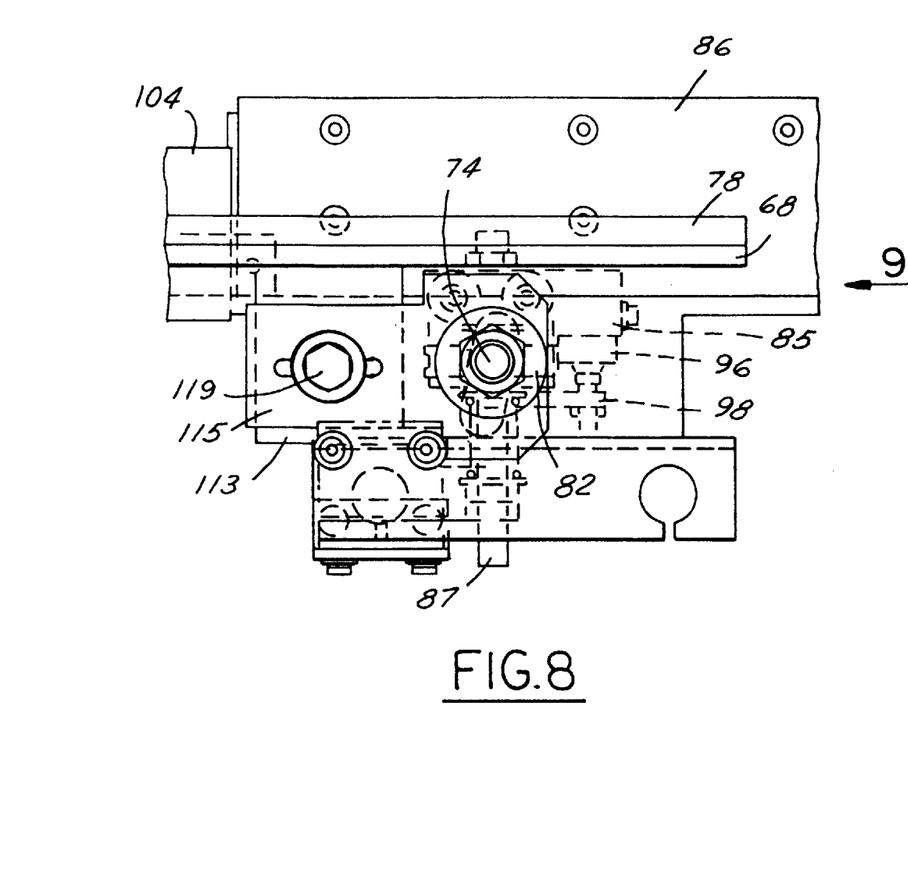
FIG. 8 is a fragmentary top plan view taken substantially from the direction 8 in FIG. 6.
Figure 9:
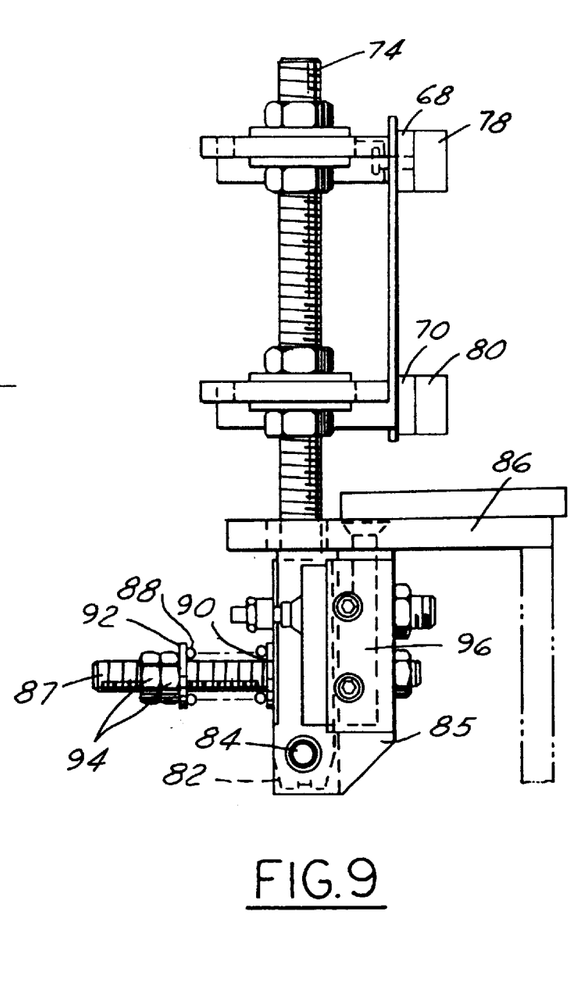
FIG. 9 is an end elevational view taken substantially from a direction 9 in FIG. 8.

Opposed to drive belt 30, including infeed reach 38, in the embodiment of FIGS. 1–10, is an abutment drag rail assembly 66. Referring in particular to FIGS. 1 and 6–9, abutment drag rail assembly 66 comprises a pair of elongated drag rails 68, 70 mounted in vertically spaced relation to each other on a pair of longitudinally spaced drag rail mounting posts 72, 74. Each drag rail 68, 70 has an angulated infeed reach 76 that is approximately parallel in assembly to infeed reach 38 of belt 30 (FIG. 1). In the preferred embodiment of the invention, the infeed reach 76 of each drag rail 68, 70 is angulated approximately one degree away from the opposing infeed reach 38 of belt 30 for enhanced funneled capture of the containers fed thereto. The elongated body of each drag rail 68, 70 is linear and parallel to the opposing elongated reach of belt 30. Each rail 68, 70 has a facing layer 78, 80 of elastomeric material, such as foam rubber, for opposed engagement by containers 22. Posts 72, 74 are threaded, and rails 68, 70 are vertically adjustably mounted thereon, as best seen in FIG. 9. The lower end of each post 72, 74 is affixed to block 82 that is pivotal on a horizontal pin 84 carried by a block 85 disposed beneath a carriage 86. A stud 87 extends horizontally from each block 85 through the associated block 82, and a coil spring 88 is captured in compression between a washer 90 abutting each block 82, and a washer 92 and a pair of nuts 94 carried by each stud 87. Springs 88 thus urge blocks 82, posts 72, 74 and drag rails 68, 70 to the right in FIG. 9, and toward belt 30 in FIG. 1. Drag rails 68, 70 and posts 72, 74 are pivotal about pins 84 away from belt 30 against the force of springs 88. The force of springs 88 resisting such pivotal motion may be adjusted by means of nuts 94. A limit switch 96 is 5 carried by each block 85 adjacent to each drag rail support post 72, 74. Each limit switch 96 is coupled to the adjacent pivot block 82 by means of a cross arm 98. Cross arms 98 normally contact and depress the actuator of each switch 96. In the event that the drag rails and mounting posts are pivoted away from drive belt 30 against the forces of springs 88 by a sufficient distance, the actuators of switches 96 are released and the switches accordingly change state.

The entire drag rail assembly 66 is mounted on carriage 86. A wear plate 104 is also mounted on carriage 86 in a position disposed beneath rails 68, 70. An elongated slot 105 (FIGS. 1 and 10) is formed by the edges of wear plate 104 and conveyor 24 as illustrated in FIG. 1. Drag rails 68, 70 are individually vertically adjustable on posts 72, 74, and are individually horizontally adjustably mounted on carriage 86 by means of the mechanism 107 illustrated in FIGS. 1, 6, 7, 14 and 15. Adjacent to the infeed reach of each drag rail 68, 70, a lower plate 106 is secured to each drag rail and extends laterally away from conveyor 24. Each lower plate 106 slidably carries an upper plate 108, which extends longitudinally from lower plate 106 to mounting post 72. Opposed nuts adjustably position upper plates 108 on mounting post 72. Each lower plate 106 has a pocket 110, and each upper plate 108 has a partcylindrical bore with threads 112 formed therein. A set screw 114 is disposed in a pocket 110 of each plate 106 in threaded engagement with threads 112 on the associated plate 108. Thus, a wrench 116 (FIG. 14) or other suitable tool may be engaged with screw 114 for adjusting the position of plate 106, and the drag rail carried thereby, with respect to plate 108 and mounting post 72. A pair of screws 117 extend through plate 108 into plate 106 for locking the plates and drag rails in adjusted position. The downstream ends of drag rails 68, 70 are longitudinally adjustably mounted with respect to post 74 by means of plates 113, 115 and screw 119 (FIGS. 1 and 8). Thus, angulated infeed reaches 76 of rails 68, 70 may be longitudinally adjusted with respect to infeed reach 38 of belt 30, while the main portions of belt 30 and rails 68, 70 remain parallel to each other over conveyor 24 and wear plate 104. This adjustment of the drag rails accommodates containers of differing diameter, and differing frictional engagement between the infeed reach 38 of belt 30 and the opposing elastomeric surfaces of the drag rails. Lateral position of the drag rails may be adjusted by means of the slots in plates 108, 115 surrounding posts 72, 74, and vertical position of the drag rails may be adjusted by means of threaded posts 72, 74 as previously described. (See FIG. 9.)

Figure 10:
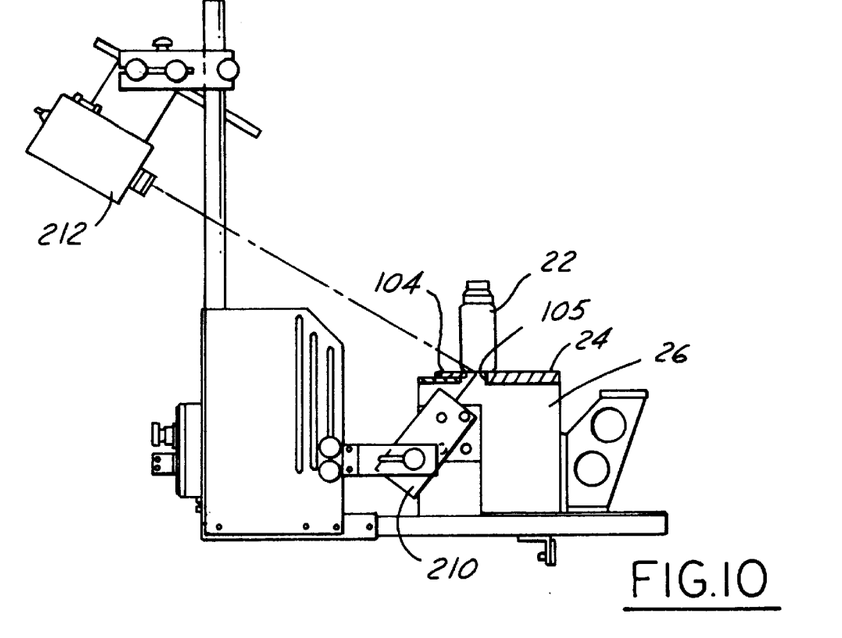
FIGS. 10 and 10A are schematic diagrams that illustrate exemplary positions of the inspection optics with respect to the inspection conveyor.

FIG. 10 illustrates disposition of an inspection light source 210 and an inspection camera 212 with respect to each other and with respect to wear plate 104 and conveyor 24. As containers 22 are diverted by infeed belt reach 38 and infeed drag rail reaches 76 laterally off of conveyor 24 so as to be supported by conveyor 24 and wear plate 104, the speed of longitudinal container motion is increased. Preferably, the speed of belt 30 is approximately 2.2 times the speed of conveyor 24, which increases the speed of the containers passing through the inspection station to about 1.1 times the conveyor speed. This slight increase in container speed ensures that there will be a slight separation between the containers, preferably on the order of one-half inch, even if the conveyors are tightly packed at the input to the inspection station. At the same time, rolling engagement between containers 22 and drag rails 68, 70, coupled with driving motion of belt 30, rotates the containers about their axes as the containers are propelled in sequence over slot 105. Light source 210 is angulated to project a line-shaped light beam through slot 105 onto the bottoms of sequential containers 22 as the containers pass over the slot. Camera 212 is mounted above and to the side of conveyor 24 and wear plate 104, and has a field of view that extends along slot 105 between the wear plate and the conveyor. In this way, light energy is refracted and/or reflected from each container 22 in sequence onto camera 212. Light source 210 is connected to a source of electrical power. Camera 212 contains an information processor 214 (FIG. 16) for analyzing the light energy received by camera 212 and obtaining appropriate information indicative of commercial variations in the containers. In this respect, operation of light source 210, camera 212 and information processor 214 preferably is as disclosed in above-noted U.S. Patent 4,874,940, assigned to the assignee hereof, the disclosure of which is incorporated herein by reference.

Figure 10A:
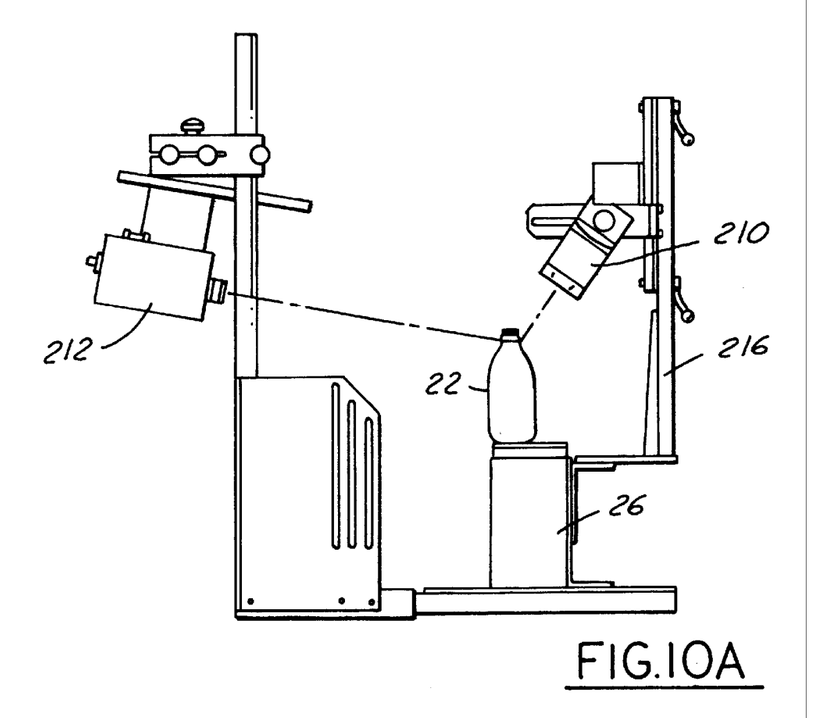

FIG. 10A illustrates an alternative inspection configuration for camera 212 and light source 210. In FIG. 10A, light source 210 is mounted on a bracket 216 above conveyor support 26, and angulated downwardly to direct light energy onto the finish of containers 22 as they pass through the inspection station. Reflected light energy is incident on camera 212 for detection of commercial variations. Numerous other light source/camera orientations and configurations may be implemented for inspecting containers for differing types of commercial variations as the containers are directed through the inspection station by the apparatus in accordance with the present invention.

An feed drive assembly 120 (FIGS. 1, 2 and 6) is mounted adjacent to the downstream end of drag rails 68, 70 (with respect to the direction of motion of conveyor 24). Outfeed drive assembly 120 includes a drive motor 122 coupled to an endless drive belt 124. Drive belt 124 is trained around spaced pulleys mounted on a carriage 126 in such a way that one elongated reach of belt 124 is parallel to the angulated reaches of outfeed drive belts 58, 60. Carriage 126 is removably mounted on a bracket 130 and laterally positionable with respect thereto by means of the adjustment handles 131. The vertical leg of bracket 130 has vertically oriented slotted openings by means of which the bracket is vertically adjustably mounted by handles 132 on conveyor support 26. Thus, outfeed drive 120 is vertically and laterally adjustable with respect to the conveyor support, and also longitudinally adjustable by means of slotted openings in the carriage assembly. Motor 122 has a speed such that the speed of belt 124 matches that of belts 58, 60, and substantially matches that of conveyor 24. Motors 32, 122 are operated by a motor controller 134 (FIG. 16), which is controlled by drag rail limit switches 96. That is, in the event that drag rail limit switches 96 indicate pivotal motion of the drag rails away from drive belt 30, motor controller 134 de-activates motors 32, 122, essentially shutting down the inspection station. The inspection station thus is shut down in the event of pivoting of the drag rails due to jamming of containers between the drag rails and the drive belt, or if the drag rails are pivoted out of position manually by an operator for inspection or other purposes.

In operation, containers 22 are presented in sequence by conveyor 24, and are brought by conveyor 24 into abutment with infeed reach 38 of drive belt 30. The drive belt slightly increases the longitudinal speed of the container, while at the same time diverting the containers in sequence laterally partially off of the conveyor. The containers are resiliently captured between drive belt 30 and drag rails 68, 70 before the containers partially leave conveyor 24, due to the angulated reach 76 of each drag rail 68, 70. Support carriage 44 prevents deflection of belt 30 away from drag rails 68, 70. With the containers thus captured while still on the conveyor, instability of the containers due to hesitation, stumbling or falling, is greatly reduced. The containers captured between belt 30 and drag rails 68, 70 are longitudinally propelled at increased velocity through the inspection station, while at the same time being rotated about their axes during passage across inspection slot 105. Carriage assembly 45 and drag rail assembly 66 are laterally adjusted with respect to conveyor 24 such that the containers 22 are centrally disposed over slot 105. After the containers have been transported over the inspection slot, they are brought into position between outfeed belts 58, 60 on assembly 45, and belt 124 on outfeed drive 120. These belts preferably are driven at substantially identical velocity, which is substantially the same as the longitudinal velocity of conveyor 24, so that the containers are no longer rotated about their axes, but are diverted in sequence back onto conveyor 24. Once again, this capturing of the containers between opposed outfeed drive belts minimizes instability of the containers during transfer back onto conveyor 24.

Figure 17A:
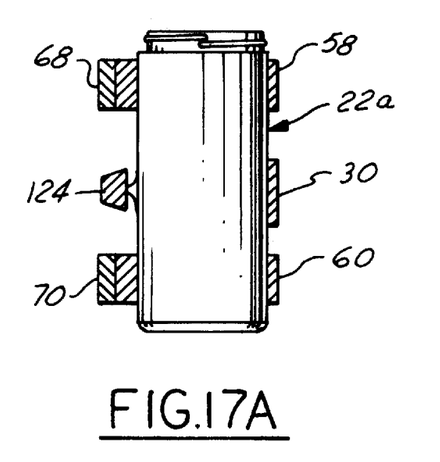
FIGS. 17A, 17B and 17C are schematic diagrams that illustrate positions of the drive belts with reference to containers of various exemplary sizes.

FIG. 17A illustrates adjusted positions for drag rails 68, 70, outfeed belts 58, 60, 124 and drive belt 30 with respect to the body of a typical container 22a, such as long jar or a long-neck bottle, having an axially elongated body. Drag rails 68, 70 are adjusted to engage vertically spaced portions of the body of the container, while drive belt 30 engages a central portion of the container body. The forces are balanced so as not to tend to tip the container. Outfeed belt 124 is positioned to engage the central portion of the body, while opposed outfeed belts 58, 60 engage the upper and lower portions of the container body, again so as to prevent tilting of the container. In this way, forces exerted on container 22a during infeed, longitudinal motion for inspection, and outfeed, are balanced with respect to the container body.

Figure 17B:
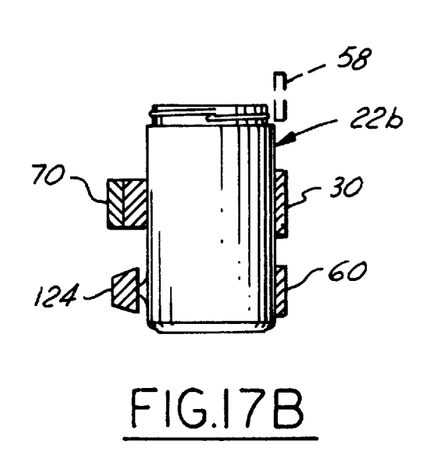
Figure 17C:
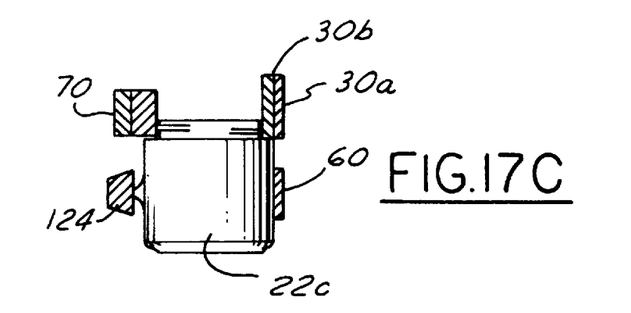

FIG. 17B illustrates belt and drag rail position for a shorter container 22b. A single drag rail 70 is employed in lateral opposition to drive belt 30, and outfeed belt 124 is laterally opposed to belt 60. FIG. 17C illustrates a set-up for use in conjunction with a babyfood container 22c, for example. Again, outfeed belts 124, 60 are opposed to each other at the lower portion of the container. Drag rail 70 engages the finish of container 22c, as does infeed drive belt 30a. Drive belt 30a has a cushion layer 30b for enhanced engagement with the container finish. By way of example, outfeed drive assembly 122 is illustrated in FIG. 2 at a position corresponding to FIGS. 17B and 17C, and in FIG. 6 at a position corresponding to FIG. 17A.

Figure 11:
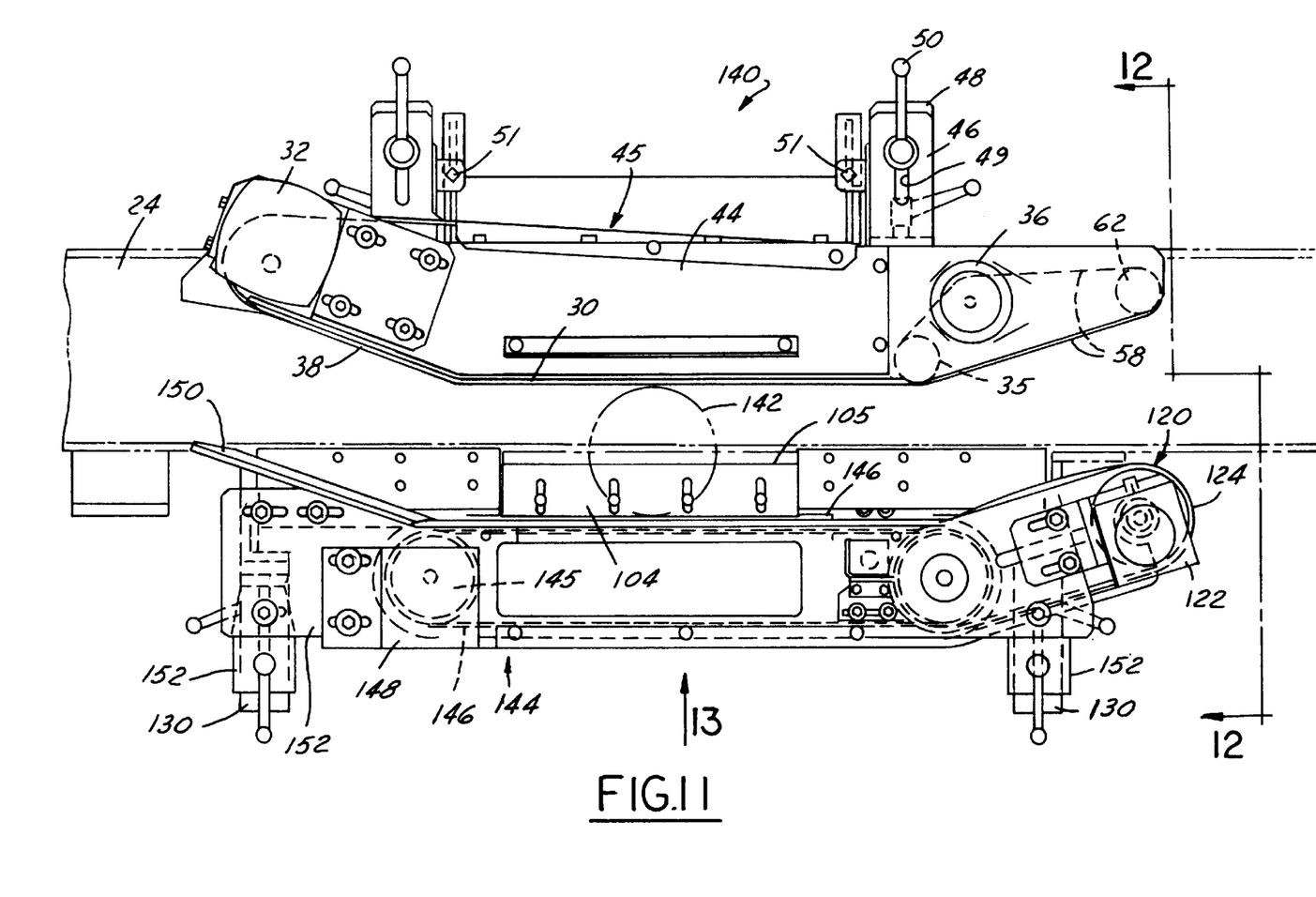
FIG. 11 is a top plan view of apparatus in accordance with a second embodiment of the invention.
Figure 12:
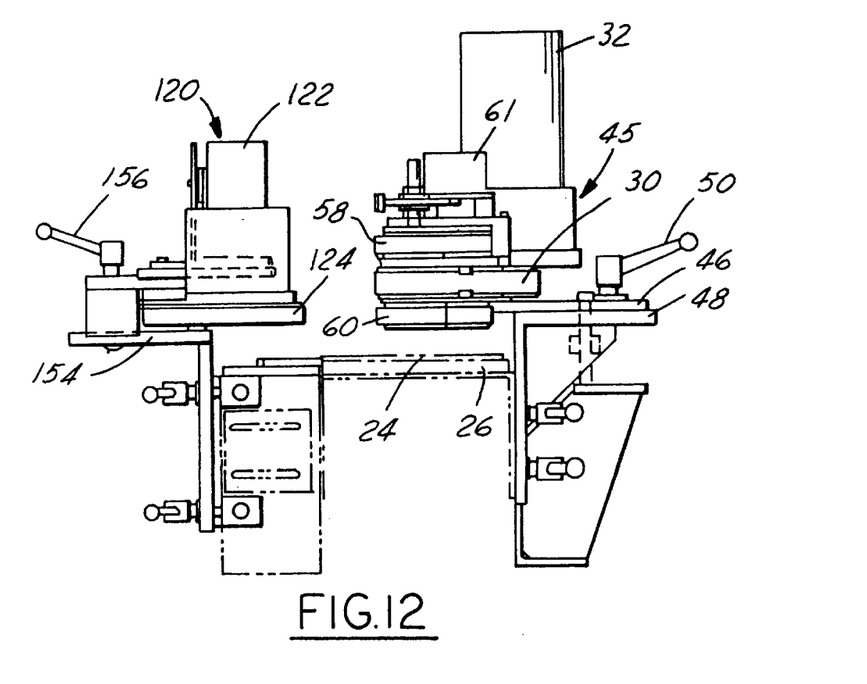
FIG. 12 is an end elevational view taken substantially from the direction 12 in FIG. 11.
Figure 13:
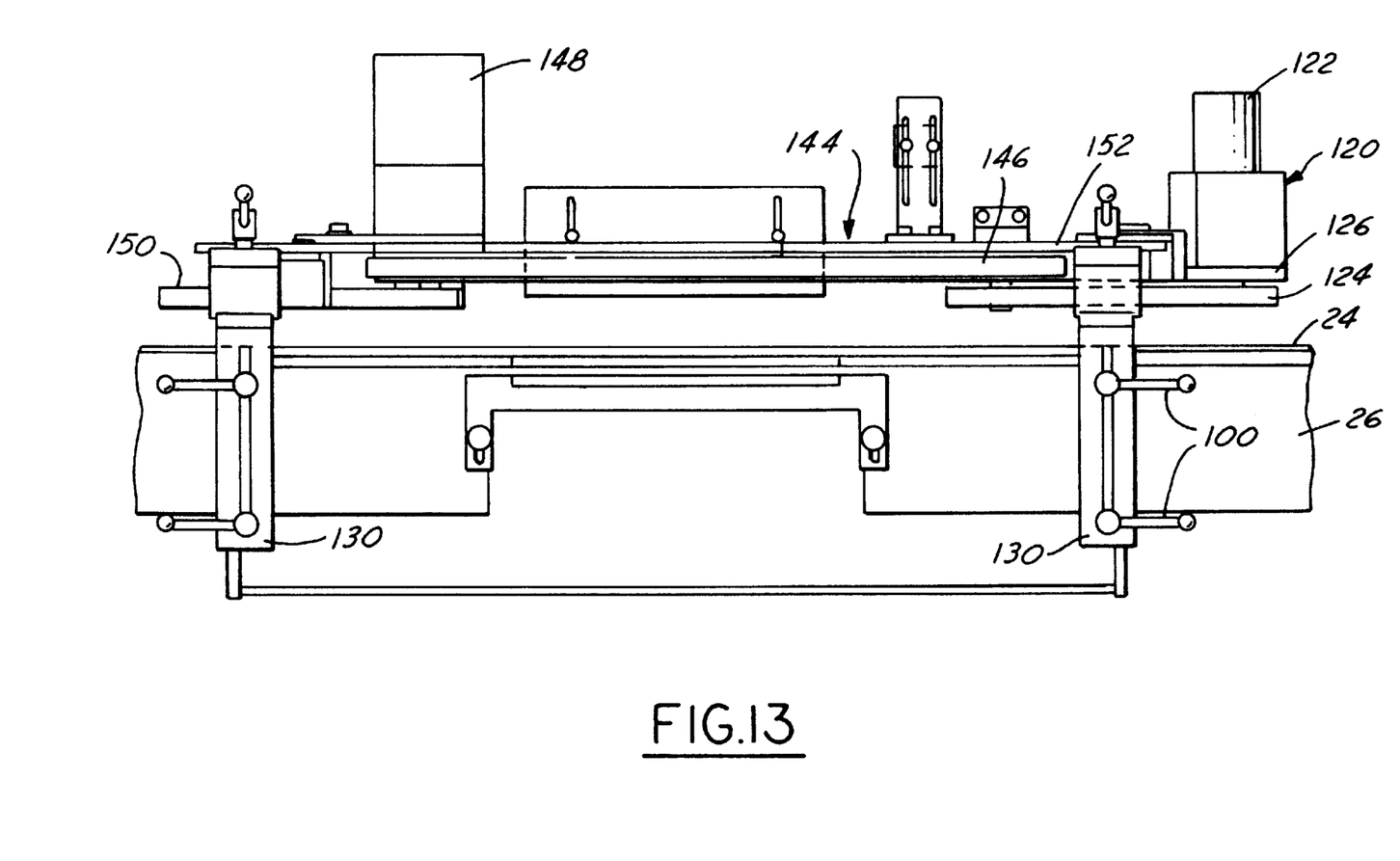
FIG. 13 is a side elevational view taken substantially from the direction 13 in FIG. 11.
Figure 14:
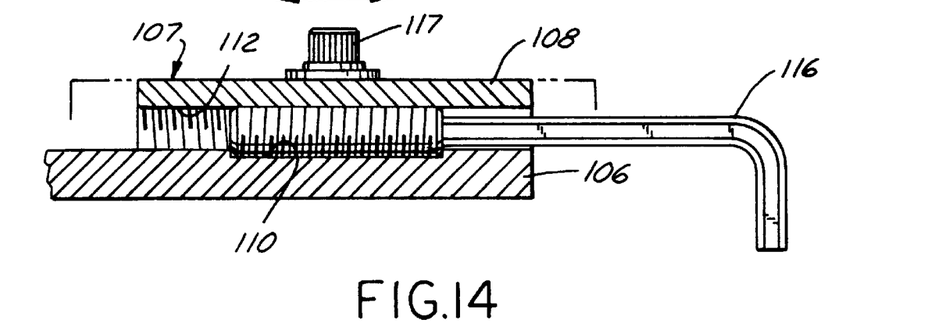
FIG. 14 is a fragmentary elevational view taken substantially from a direction 14 in FIG. 7.
Figure 15:
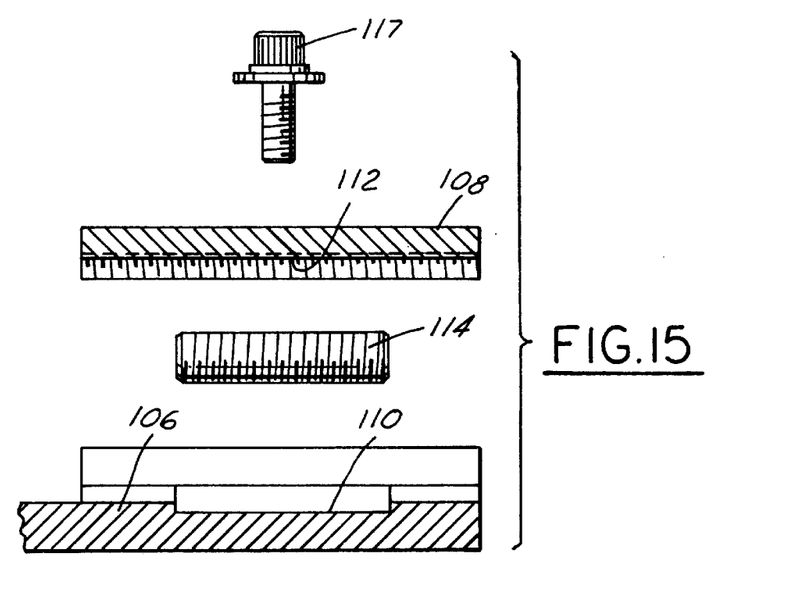
FIG. 15 is an exploded elevational view of the drag rail adjustment mechanism illustrated in FIG. 14.
Figure 16:
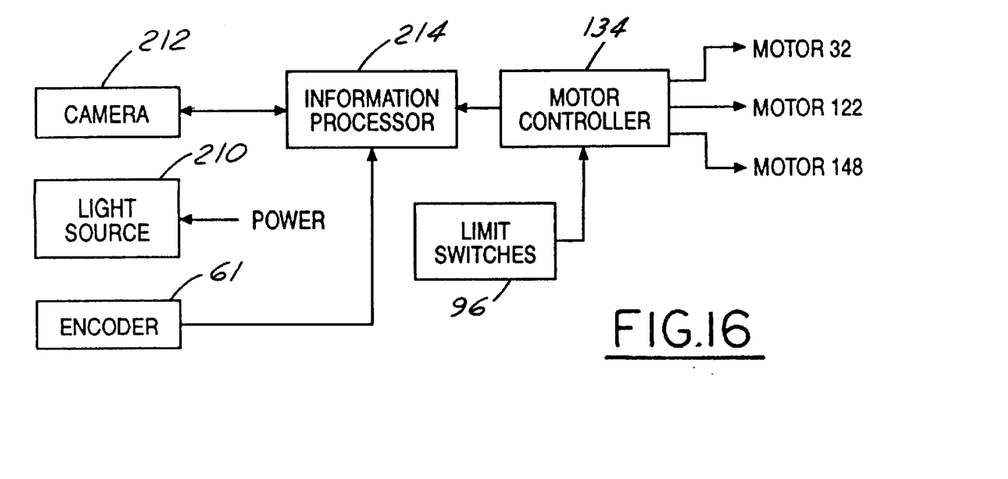
FIG. 16 is a functional block diagram of electronics for operating the inspection apparatus in accordance with the present invention.

FIGS. 11–13 illustrate a modified apparatus 140 in accordance with an embodiment of the invention that is particularly useful in conjunction with large containers such as jars. Reference numerals identical to those used in FIGS. 1–10 indicate identical parts or components. Carriage assembly 45, including drive belt 30 and motor 32 on carriage 44, is the same as in the prior embodiment, but is adjustably positioned with respect to conveyor 24 farther away from inspection slot 105, as shown in FIG. 11. Again, the purpose of this adjustment is to place the diameter of container 142 over slot 105. An opposing abutment assembly 144 includes a drive belt 146 that is trained around a pair of spaced pulleys 145, one of which is coupled to a drive motor 148 (FIGS. 11–13 and 16). Belt 146 has one longitudinal reach opposed to the longitudinal reach of belt 30 and spaced therefrom on an opposing side of inspection slot 105. Belt 146 is driven by motor 148 in a direction opposite to that of belt 30. An angulated drag rail 150 extends upstream from belt 146 at an angle opposed to the infeed reach 38 of belt 30. At the downstream end of abutment assembly 144, there is an outfeed drive assembly 120 identical to that previously described. The entire abutment assembly 144, including drive belt 146 with associated motor 148, angulated drag rail 150 and outfeed drive 120, is mounted on a carriage 152 that is mounted on conveyor support 26 by means of brackets 154 and handles 100. Larger containers 142, due to their increased diameter versus axial length, tend to exhibit less instability during infeed and outfeed with respect to conveyor 24. However, because of the larger diameters, the speed of rotation must be increased during passage across inspection slot 105 so that the container rotates at least 360° during inspection. The speeds of belts 30 and 146 are adjusted to increase the speed of rotation of the containers and slightly to increase the speed of longitudinal motion so as to ensure that there is spacing (preferably at least one-half inch) between the containers as they traverse the inspection station.

There have thus been disclosed two embodiments of the present invention that fully satisfy the objects and aims previously set forth. Infeed and outfeed of containers from and to the linear conveyor are both motor-driven while the containers are captured between opposing elements, which greatly decreases instability of the containers during transition from and to the conveyor, which in turn decreases the likelihood that a container will topple on the conveyor or in the inspection apparatus. In the embodiment of FIGS. 1–10, the spring-loaded drag rails with limit switches provide a rapid means for selectively removing ware from the inspection apparatus in the event of jam or for any other reason, and automatically terminate operation of the inspection apparatus in the event of a container misfeed. The drag rails are adjustable on-the-fly longitudinally of the conveyor for accommodating containers of differing size and differing operating conditions. A double-drive belt arrangement is provided for use in conjunction with ware of greater diameter, without sacrificing any of the stability or other advantages of the invention. The various container drive and abutment mechanism are mounted on associated carriages for ease of assembly, and may be readily retrofitted onto existing conveyor systems.

What is claimed is:

1. Apparatus for inspecting in sequence containers traveling on a linear conveyor comprising:

infeed means including a first endless drive belt having a portion overlying the conveyor for abutting engagement by containers in sequence traveling on the conveyor and a first motor driving said belt for diverting the containers laterally at least partially off of the conveyor, said first endless drive belt having an elongated reach parallel to the conveyor and an angulated reach extending over the conveyor for intercepting containers on the conveyor, abutment means disposed in opposition to said first belt for abutting engagement by containers diverted by said infeed means, such that containers diverted from the conveyor and engaged between said first belt and said abutment means are rotated during travel along said abutment means, means for optically inspecting the containers as they are rotated during travel along said abutment means, and outfeed means disposed adjacent to said abutment means for engaging containers in sequence following engagement with said abutment means and diverting the containers back onto the conveyor.

2. The apparatus set forth in claim 1 wherein said outfeed means includes a second endless belt and a second motor for diverting containers in sequence back onto the conveyor while reducing speed of the containers substantially to match that of the conveyor.

3. The apparatus set forth in claim 1 wherein said abutment means comprises a rail mounted for lateral motion in opposition to said first belt, and means resiliently urging said rail toward said first belt.

4. The apparatus set forth in claim 1 wherein said abutment means comprises a second drive belt and a second motor for driving said second belt in a direction opposite said first belt for increasing speed of rotation of the containers as they pass said inspecting means.

5. The apparatus set forth in claim 1 further comprising a second drive belt operatively coupled to said first drive belt and said first motor, and opposed to said outfeed means, for diverting containers back onto the conveyor.

6. The apparatus set forth in claim 5 wherein said outfeed means includes a third endless belt, and means driving said third belt for engaging containers between said second and third belts and diverting the containers in sequence back onto the conveyor while reducing the speed of the containers substantially to match that of the conveyor.

7. The apparatus set forth in claim 6 further comprising means coupling said second belt to said first belt for driving said second belt at a speed less than that of said first belt.

8. The apparatus set forth in claim 7 wherein said means driving said third belt comprises a second motor.

9. The apparatus set forth in claim 8 wherein said first and third belts, said first motor and said means coupling said second belt to said first belt are mounted on a carriage that is adjustably positionable with respect to the conveyor.

10. Apparatus for inspecting in sequence transparent containers traveling on a linear conveyor comprising:

infeed means overlying said conveyor for engaging containers in sequence traveling on said conveyor, including a first endless belt and a first motor driving said belt for diverting the containers laterally at least partially off of said conveyor, abutment means disposed in opposition to said first belt for engaging containers diverted by said infeed means, such that containers diverted from said conveyor and engaged between said first belt and said abutment means are rotated during travel along said abutment means, said abutment means comprising a rail mounted for lateral motion in opposition to said first belt, means resiliently urging said rail toward said first belt, and means responsive to motion of said rail away from said first belt for indicating potential jam of containers in said apparatus, means for optically inspecting the containers as they are rotated during travel along said abutment means, and outfeed means disposed adjacent to said abutment means for engaging containers in sequence following engagement with said abutment means and diverting the containers back onto the conveyor.

11. The apparatus set forth in claim 10 further comprising means coupled to said motion-responsive means for terminating operation of said first motor.

12. The apparatus set forth in claim 11 wherein said motion-responsive means comprises limit switch means.

13. The apparatus set forth in claim 10 further comprising means for adjusting position of said rail longitudinally with respect to said conveyor.

14. The apparatus set forth in claim 13 wherein said adjusting means comprises first and second plates for operative coupling in fixed position and to said rail respectively, one of said plates having surface threads and another of said plates having a surface pocket opposed to said threads, and threaded adjustment means disposed in said pocket with threads in engagement with said surface threads.

15. A method of inspecting containers traveling on a linear conveyor at a first speed, comprising the steps of:
(a) positioning a first motor-driven belt overlying the conveyor to divert containers from the conveyor laterally against an abutment means,
(b) transporting the containers between the first belt and the abutment means at a second speed greater than said first speed while rotating the containers,
(c) optically inspecting the containers during said step (b), and then
(d) diverting the containers in sequence between second and third motor-driven belts back onto the conveyor at a speed substantially matching said first speed.

16. The method set forth in claim 15 comprising the additional step of:
(e) providing as said abutment means a fourth motor-driven belt traveling in a direction opposite said first belt for increasing speed of rotation of the containers in said step (b).

17. The method set forth in claim 15 comprising the additional steps of:
(e) providing a rail as said abutment means,
(f) resiliently urging said rail toward said first belt, and
(g) detecting potential jam of containers between said abutment rail and said first belt as a function of motion of said rail away from said first belt.

18. The method set forth in claim 17 comprising the additional step of:

(h) terminating operation of said first belt responsive to said step (g).

19. Apparatus for inspecting in sequence containers traveling on a linear conveyor comprising:
infeed means including a first endless drive belt having a portion overlying the conveyor for abutting engagement by containers in sequence traveling on the conveyor and a first motor driving said belt for diverting the containers laterally at least partially off of the conveyor, abutment means disposed in opposition to said first belt for abutting engagement by containers diverted by said infeed means, such that containers diverted from the conveyor and engaged between said first belt and said abutment means are rotated during travel along said abutment means, means for optically inspecting the containers as they are rotated during travel along said abutment means, and outfeed means disposed adjacent to said abutment means for engaging containers in sequence following engagement with said abutment means and diverting the containers back onto the conveyor, said outfeed means including a second endless belt and a second motor for diverting containers in sequence back onto the conveyor while reducing speed of the containers substantially to match that of the conveyor.

20. The apparatus set forth in claim 19 wherein said first endless drive belt has an elongated reach parallel to the conveyor and an angulated reach extending over the conveyor for intercepting containers on the conveyor.

21. The apparatus set forth in claim 19 wherein said second endless belt and said second motor are mounted on a carriage that is adjustably positionable with respect to the conveyor.

22. Apparatus for inspecting in sequence containers traveling on a linear conveyor comprising:
infeed means including a first endless drive belt having a portion overlying the conveyor for abutting engagement by containers in sequence traveling on the conveyor and a first motor driving said belt for diverting the containers laterally at least partially off of the conveyor, abutment means disposed in opposition to said first belt for abutting engagement by containers diverted by said infeed means, such that containers diverted from the conveyor and engaged between said first belt and said abutment means are rotated during travel along said abutment means, said abutment means comprising a rail mounted for lateral motion in opposition to said first belt, and means resiliently urging said rail toward said first belt, means for optically inspecting the containers as they are rotated during travel along said abutment means, and outfeed means disposed adjacent to said abutment means for engaging containers in sequence following engagement with said abutment means and diverting the containers back onto the conveyor.

23. The apparatus set forth in claim 22 comprising first and second rails vertically spaced from each other.

24. The apparatus set forth in claim 22 further comprising elastomeric means on said rail for resilient engagement with containers.

25. The apparatus set forth in claim 22 wherein said abutment means comprises means mounting said rail for pivotal motion away from said first belt.

26. The apparatus set forth in claim 25 wherein said pivotal mounting means comprises a pair of posts spaced from each other longitudinally of said rail, and wherein said resiliently urging means comprises a spring in engagement with each of said posts.

27. The apparatus set forth in claim 26 further comprising means for adjusting force of said spring urging said rail toward said first belt.

28. The apparatus set forth in claim 22 further comprising means responsive to motion of said rail away from said first belt for indicating potential jam of containers in said apparatus.

29. The apparatus set forth in claim 28 wherein said motion-responsive means comprises limit switch means.

30. The apparatus set forth in claim 29 further comprising means operatively coupling said limit switch means to said first motor for terminating operation of said first motor upon operation of said limit switch means.

31. The apparatus set forth in claim 22 wherein said first drive belt has an angulated infeed reach extending over the conveyor for intercepting containers on the conveyor, and wherein said rail has an angulated infeed reach opposed to said angulated infeed reach of said first belt.

32. The apparatus set forth in claim 31 wherein said rail further includes means for adjusting position of said infeed reach of said rail with respect to said infeed reach of said first belt in the direction of motion of the conveyor for accommodating containers of differing diameters.

33. The apparatus set forth in claim 32 wherein said adjusting means comprises first and second plates for operative coupling in fixed position and to said rail respectively, one of said plates having surface threads and another of said plates having a surface pocket opposed to said threads, and threaded adjustment means disposed in said pocket with threads in engagement with said surface threads.

34. The apparatus set forth in claim 33 wherein said adjustment means further comprises means for locking said plates in adjusted position.

35. The apparatus set forth in claim 34 wherein said adjusting means is disposed adjacent to an infeed end of said rail, and further comprising means for slidably supporting an outfeed end of said rail for accommodating longitudinal adjustment of said rail.

36. Apparatus for inspecting in sequence containers traveling on a linear conveyor comprising:

infeed means including a first endless drive belt having a portion overlying the conveyor for abutting engagement by containers in sequence traveling on the conveyor and a first motor driving said belt for diverting the containers laterally at least partially off of the conveyor, abutment means disposed in opposition to said first belt for abutting engagement by containers diverted by said infeed means, such that containers diverted from the conveyor and engaged between said first belt and said abutment means are rotated during travel along said abutment means, means for optically inspecting the containers as they are rotated during travel along said abutment means, said abutment means comprising a second drive belt and a second motor for driving said second belt in a direction opposite to that of said first belt for increasing speed of rotation of the containers as they pass said inspecting means, and outfeed means disposed adjacent to said abutment means for engaging containers in sequence following engagement with said abutment means and diverting the containers back onto the conveyor.

37. The apparatus set forth in claim 36 wherein said second drive belt and said second motor are mounted on a carriage that is adjustably positionable with respect to the conveyor.

* * * * *